United States Patent
Yi et al.

(10) Patent No.: US 8,989,344 B2
(45) Date of Patent: Mar. 24, 2015

(54) SYSTEM AND METHOD FOR MEASURING ASH CONTENT AND CALORIFIED VALUE OF COAL

(71) Applicant: Tsinghua University, Beijing (CN)

(72) Inventors: Hongchang Yi, Beijing (CN); Qian Lin, Beijing (CN); Jianping Cheng, Beijing (CN)

(73) Assignee: Tsinghua University (CN)

( * ) Notice: Subject to any disclaimer, the term of this patent is extended or adjusted under 35 U.S.C. 154(b) by 267 days.

(21) Appl. No.: 13/722,014

(22) Filed: Dec. 20, 2012

(65) Prior Publication Data

US 2013/0188776 A1 Jul. 25, 2013

(30) Foreign Application Priority Data

Dec. 31, 2011 (CN) .......................... 2011 1 0460686

(51) Int. Cl.
*G01N 23/223* (2006.01)
*G01N 23/087* (2006.01)
*G01N 23/20* (2006.01)

(52) U.S. Cl.
CPC ................................ *G01N 23/20091* (2013.01)
USPC .................. 378/53; 378/44; 378/45; 378/46; 378/98.9

(58) Field of Classification Search
CPC .......... C10L 9/00; G01N 22/04; G01N 23/223
USPC .................................. 378/44, 45, 46, 53, 98.9
See application file for complete search history.

(56) References Cited

U.S. PATENT DOCUMENTS

| | | | | |
|---|---|---|---|---|
| 6,130,931 | A | * 10/2000 | Laurila et al. | 378/45 |
| 8,306,188 | B2 | * 11/2012 | Klein | 378/98.9 |
| 2010/0303201 | A1 | 12/2010 | Klein | |
| 2013/0101087 | A1 | * 4/2013 | Yi et al. | 378/53 |

* cited by examiner

*Primary Examiner* — Nikita Wells
(74) *Attorney, Agent, or Firm* — Lerner, David, Littenberg, Krumholz & Mentlik, LLP

(57) ABSTRACT

A system and a method for measuring an ash content and a calorific value of a coal are provided. The system comprises: an X ray device, disposed over the coal and configured to emit an X ray to the coal; at least one X ray measuring device, disposed over the coal and configured to measure an energy spectrum of an X ray reflected by the coal; a distance sensor, disposed over the coal and configured to measure a distance between the coal and the at least one X ray measuring device; and a computing device, configured to receive the energy spectrum and the distance from the at least one X ray measuring device and the distance sensor and to compute the ash content and the calorific value of the coal according to the energy spectrum and the distance.

16 Claims, 1 Drawing Sheet

SYSTEM AND METHOD FOR MEASURING ASH CONTENT AND CALORIFIED VALUE OF COAL

CROSS REFERENCE TO RELATED APPLICATION

This application claims priority to and benefits of Chinese Patent Application No. 201110460686.9, filed with State Intellectual Property Office, P. R. C. on Dec. 31, 2011, the entire content of which is incorporated herein by reference.

FIELD

Embodiments of the present disclosure generally relate to a coal detection field, and more particularly, to a system and a method for measuring an ash content and a calorific value of a coal.

BACKGROUND

An ash content and a calorific value are important property parameters of a coal, in which the calorific value of the coal may be computed by the ash content. Therefore, a technology for online measuring the ash content of the coal is of importance in a coal detection field. A traditional method for measuring the ash content of the coal generally uses a radiometric technology, such as a low-energy gamma ray back scattering method, a high-energy gamma ray electron pair effect, a natural gamma ray measuring method, a dual-energy gamma ray transmission method and a neutron activation prompt gamma analysis method.

The low-energy gamma ray back scattering method, the high-energy gamma ray electron pair effect, and the natural gamma ray measuring method are proved to be not suitable for measuring the ash content due to respective limitation, and thus they are not used widely.

The neutron activation prompt gamma analysis method can analyze element compositions of the coal, and then can measure the ash content and multiple different element contents of the coal according to the analysis. However, a device used for the neutron activation prompt gamma analysis method is very expensive. Moreover, a service life of a neutron source (such as californium-252) or a neutron tube used by the device is very short and needed to be regularly replaced, which further increase costs. In addition, a measuring accuracy of the neutron activation prompt gamma analysis method is actually not higher than that of the dual-energy gamma ray transmission method. Therefore, the neutron activation prompt gamma analysis method is not suitable for a large scale industrial application.

Currently, the dual-energy gamma ray transmission method is the most widely used method for measuring the ash content of the coal. Comparing to other methods above, the dual-energy gamma ray transmission method has advantages of being adapted for measuring coals with different particle sizes, thicknesses and densities. However, the measuring result of the dual-energy gamma ray transmission method is limited by the element compositions of the coal. In addition, the method uses a radioisotope as a radioactive source, which may do damage to an environment due to leakage during usage, transportation and decommission.

SUMMARY

Embodiments of the present disclosure seek to solve at least one of the problems existing in the prior art to at least some extent.

According to embodiments of a first broad aspect of the present disclosure, there is provided a system for measuring an ash content and a calorific value of a coal. The system comprises: an X ray device, disposed over the coal and configured to emit an X ray to the coal; at least one X ray measuring device, disposed over the coal and configured to measure an energy spectrum of an X ray reflected by the coal; a distance sensor, disposed over the coal and configured to measure a distance between the coal and the at least one X ray measuring device; and a computing device, connected with the at least one X ray measuring device and the distance sensor respectively, and configured to receive the energy spectrum of the X ray reflected by the coal and the distance between the coal and the at least one X ray measuring device and to compute the ash content and the calorific value of the coal according to the energy spectrum and the distance.

In one embodiment of the present disclosure, the X ray emitted by the X ray device comprises a bremsstrahlung X ray with a continuous energy.

In one embodiment of the present disclosure, the system further comprises a standard block, in which during a conveyance of the coal on a conveyer belt, the standard block is taken away to make the X ray emitted by the X ray device directly incident on the coal and to make the X ray reflected by the coal directly reach the at least one X ray measuring device; and when the conveyance of the coal on the conveyer belt is suspended, the standard block is disposed between the conveyer belt and the X ray device and between the conveyer belt and the at least one X ray measuring device to make the X ray emitted by the X ray device incident on the standard block so that the at least one X ray measuring device measures an energy spectrum of an X ray reflected by the standard block to correct an energy spectrum change of the X ray emitted by the X ray device. Therefore, the measuring accuracy of the ash content may be further increased.

In one embodiment of the present disclosure, the X ray measuring device comprises: an X ray detector, configured to detect the X ray reflected by the coal and to output a corresponding signal; a high voltage power source, configured to supply a power to the X ray detector; and a signal collector, configured to receive and reshape the corresponding signal and to generate the energy spectrum of the X ray reflected by the coal according to the corresponding signal.

In one embodiment of the present disclosure, the X ray detector comprises any one of a scintillation detector, a proportional counter, a semiconductor detector and a combination thereof.

In one embodiment of the present disclosure, a window of the scintillation detector is a beryllium window.

In one embodiment of the present disclosure, an energy resolution of the semiconductor detector is larger than 250 eV.

In one embodiment of the present disclosure, the signal collector comprises any one of a multi-channel pulse amplitude analyzer, a single-channel pulse amplitude analyzer, a voltage comparator and a combination thereof.

In one embodiment of the present disclosure, the X ray device comprises an X ray tube with a working voltage ranging from 10 kV to 200 kV.

In one embodiment of the present disclosure, the X ray tube comprises a silver target.

In one embodiment of the present disclosure, the system further comprises a detecting box with the ray device and the at least one X ray measuring device disposed inside.

In one embodiment of the present disclosure, a minimum distance between an upper surface of the coal and a lower surface of the detecting box is 2 cm.

In one embodiment of the present disclosure, the system further comprises a heating and cooling device disposed in the detecting box and connected with the computing device, in which the computing device controls the heating and cooling device to keep a temperature of the detecting box constant.

According to embodiments of a second broad aspect of the present disclosure, there is provided a method for measuring an ash content and a calorific value of a coal by a system. The system comprises an X ray device, at least one X ray detecting device, a distance sensor and a computing device, wherein the X ray device, the at least one X ray measuring device and the distance sensor are disposed over the coal, and the computing device is connected with the at least one X ray measuring device and the distance sensor respectively. The method comprises steps of: S01: emitting an X ray to the coal by the X ray device; S02: measuring an energy spectrum of an X ray reflected by the coal by the at least one X ray measuring device; S03: measuring a distance between the coal and the at least one X ray measuring device by the distance sensor; and S04: computing the ash content and the calorific value of the coal by the computing device according to the distance and the energy spectrum.

In one embodiment of the present disclosure, the X ray emitted by the ray device comprises a bremsstrahlung X ray with a continuous energy.

In one embodiment of the present disclosure, the method further comprises the steps of: when a conveyance of the coal on a conveyor belt is suspended, disposing a standard block between the conveyor belt and the X ray device and between the conveyer belt and the at least one X ray measuring device to make the X ray emitted by the X ray device incident on the standard block; measuring an energy spectrum of an X ray reflected by the standard block by the at least one X ray measuring device; and correcting an energy spectrum change of the X ray emitted by the X ray device according to the energy spectrum of the X ray reflected by the standard block.

With the system and the for measuring the ash content and the calorific value of the coal according to embodiments of the present disclosure, a conventional radiation source is replaced with the X ray device, which does not emit any X ray when an power is turned off, and thus a security is improved. Furthermore, by using the X ray with the continuous energy emitted by the X ray device and by measuring the energy spectrums of the X ray with different energies reflected by the coal, an influence of changes of a thickness and a high atomic number element ratio of the coal on the ash content and the calorific value may be corrected, and thus a measuring accuracy may be increased. In addition, by measuring the distance between the coal and the at least one X ray measuring devices by the distance sensor, an influence of a change of the thickness of the coal on the ash content and the calorific value may also be corrected, and thus the measuring accuracy may be further increased.

The above summary of the present disclosure is not intended to describe each disclosed embodiment or every implementation of the present disclosure. The Figures and the detailed description which follow more particularly exemplify illustrative embodiments.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
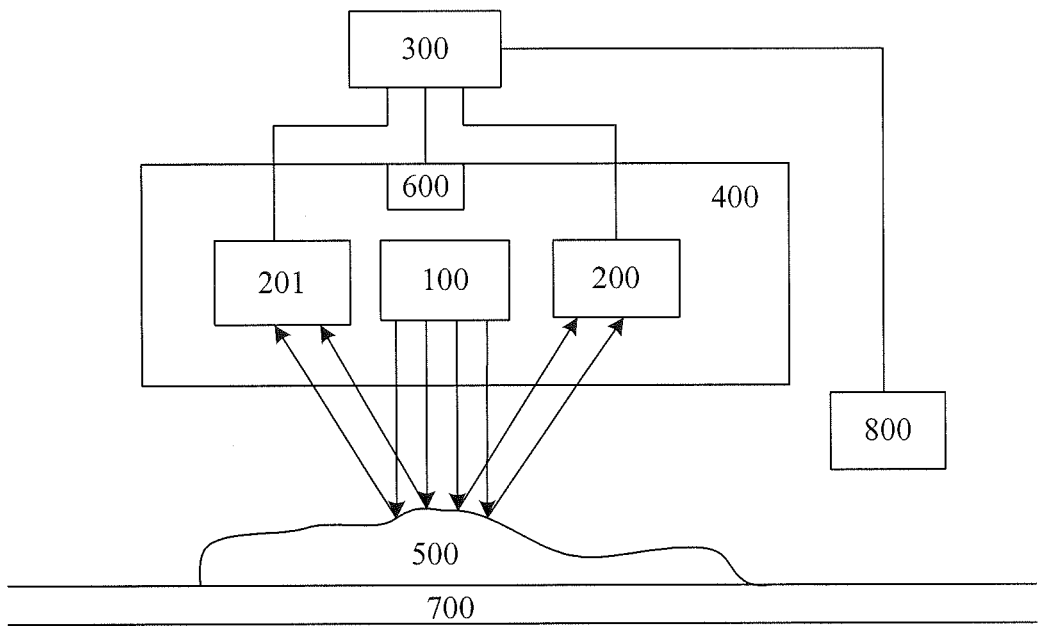
FIG. 1 is a schematic view of a system for measuring an ash content and a calorific value of a coal according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

Various embodiments and examples are provided in the following description to implement different structures of the present disclosure. In order to simplify the present disclosure, certain elements and settings will be described. However, these elements and settings are only examples and are not intended to limit the present disclosure. In addition, reference numerals may be repeated in different examples in the disclosure. This repeating is for the purpose of simplification and clarity and does not refer to relations between different embodiments and/or settings. Furthermore, examples of different processes and materials are provided in the present disclosure. However, it would be appreciated by those skilled in the art that other processes and/or materials may be also applied. Moreover, a structure in which a first feature is "on" a second feature may include an embodiment in which the first feature directly contacts the second feature and may include an embodiment in which an additional feature is prepared between the first feature and the second feature so that the first feature does not directly contact the second feature.

Further, in the description, unless indicated otherwise, "a plurality of" refers to two or more.

FIG. 1 is a schematic view of a system for measuring an ash content and a calorific value of a coal according to an embodiment of the present disclosure. As shown in FIG. 1, the system comprises an X ray device 100, X ray measuring devices 200 and 201, a distance sensor 800 and a computing device 300.

The X ray device 100 is disposed over an coat 500 and configured to emit an X ray to the coal 500. The X ray measuring devices 200 and 201 are disposed over the coal 500 and configured to measure an energy spectrum of an X ray reflected by the coal 500. It should be noted that, a number of the X ray measuring devices shown in FIG. 1 is explanatory and illustrative, and shall not be construed to limit the present disclosure. The distance sensor 800 is disposed over the coal 500 and configured to measure a distance between the coal 500 and the X ray measuring devices 200, 201. The computing device 300 is connected with the X ray measuring devices 200, 201 and the distance sensor 300 respectively and configured to receive the energy spectrum of the X ray reflected by the coal 500 and the distance between the coal 500 and the X ray measuring devices 200, 201 and to compute the ash content and the calorific value of the coal 500 according to the energy spectrum and the distance.

In one embodiment, the X ray emitted by the X ray device 100 is preferably a bremsstrahlung X ray with a continuous energy. As the X ray device 100 emits the X ray with the continuous energy and attenuation coefficients of the X ray with different energies are different, a plurality of different energy spectrums (i.e., intensities) of the X ray may be detected by the X ray measuring devices 200 and 201. Further, as the intensity of the X ray reflected by the coal 500 has an approximate inversely proportional relationship with the ash content of the coal 500 and has an approximate directly proportional relationship with the thickness of the coal 500, by using the X ray with the continuous energy, a plurality of equations about a relation between the intensity of the X ray reflected by the coal 500 and the ash content of the coal 500 and a relation between the intensity of the X ray reflected by the coal 500 and the thickness of the coal 500 may be obtained. Then, with a constant thickness of the coal 500 during the same measurement, the ash content of the coal 500 may be obtained by solving these equations. However, the intensity of the X ray reflected by the coal 500 may also relates with the distance between a reflection point and the X ray measuring devices 200, 201, that is, the intensity of the X ray reflected by the coal 500 has an approximate inversely proportional relationship with a square of the distance. This is because the X ray reflected by the coal 500 may be in every direction, and thus the nearer the distance between the coal 500 and the X ray measuring devices 200, 201 is, the more the X rays enter into the X ray measuring devices 200, 201. Then, when the intensity of the X ray reflected by the coal 500 changes, it is hard to judge whether it is caused by the change of the ash content or the change of the thickness of the coal 500. In the present disclosure, by measuring the distance between the coal 500 and the X ray measuring devices 200, 201 with the distance sensor 800, the intensity of the X ray reflected by the coal 500 is corrected and then the ash content of the coal 500 is obtained.

In addition, if the X ray with a low energy is used as the radiation source, the intensity of the X ray reflected by the coal 500 will be attenuated by the air during reflecting back to the X ray measuring devices 200, 201 from the coal 500. Then, by measuring the distance between the coal 500 and the X ray measuring devices 200, 201, this attenuation may be corrected according to an exponential attenuation law of the X ray, and the measuring accuracy may be increased.

Furthermore, as the system according to the present disclosure replaces the traditional radioactive source with the X ray device, which does not emit the X ray when a power is turned off, the security may also be improved.

From the above description, it can be seen that the more the X ray measuring devices are used, the more X rays reflected by the coal are detected, and thus the higher the measuring accuracy is. But if only using one X ray measuring device, it is also possible to detect a plurality of X rays. Therefore, the system according the present disclosure may comprise at least one X ray measuring device.

In one embodiment, the X ray device 100 may be an X ray tube, which has a more simple structure and a lower price than an accelerator. Furthermore, a working voltage of the X ray tube may range from 10 kV to 200 kV, which is preferably 20 kV. Moreover, the X ray tube may use a silver target. As silver has an excellent thermal conductivity which is beneficial for the X ray tube to dissipate heat, a service life of the X ray tube may be prolonged.

In one embodiment, the X ray measuring device 200 may comprise an X ray detector, a high voltage power source and a signal collector. The high voltage power source is configured to supply a power to the X ray detector, and voltages of the high voltage power source may differ from dozens of volts to thousands of volts for different X ray detectors. The X ray detector is configured to detect the X ray reflected by the coal 500 and to output a corresponding signal. The signal collector is configured to receive and reshape the corresponding signal and to generate the energy spectrum of the X ray reflected by the coal according to the corresponding signal.

In some embodiments, the X ray detector may be a scintillation detector. A window of the scintillation detector may preferably be a beryllium window, because beryllium absorbs very little X ray so as to allow X ray with low energy to pass through the window. In another embodiment, the X ray detector may also be a directly proportional counter or a semiconductor detector. In general, the larger an energy resolution of the semiconductor detector is, the weaker a resolving ability for X rays with different energies is. However, the weaker the resolving ability of the semiconductor detector is, the lower a cost thereof is. Therefore, in one embodiment, the energy resolution of the semiconductor detector is chosen to be larger than 250 eV.

Furthermore, in one embodiment, the signal collector may comprise any one of a multi-channel pulse amplitude analyzer, a single-channel pulse amplitude analyzer, a voltage comparator and a combination thereof.

Further, it is found that as the energy spectrum of the X ray emitted by the X ray device 100 may change during long term usage, the energy spectrum of the X ray reflected by the coal 500 may also change accordingly, which may affect the measurement of the ash content. Thus, in one embodiment, the system may further comprise a standard block (not shown in FIG. 1). During a conveyance of the coal 500 on a conveyer belt 700, the standard block is taken away (for example, is raised up) to make the X ray emitted by the X ray device 100 directly incident on the coal 500 and to make the X ray reflected by the coal 500 directly reach the X ray measuring devices 200, 201; and when the conveyance of the coal 500 on the conveyer belt 700 is suspended, the standard block is disposed between the conveyer belt 700 and the X ray device 100 and between the conveyer belt 700 and the X ray measuring devices 200, 201 to make the X ray emitted by the X ray device 100 incident on the standard block. Therefore, it is possible to derive an energy spectrum change of the X ray emitted by the X ray device 100 by comparing the energy spectrums of the X ray reflected by the standard block within different periods of time, and thus the energy spectrum change of the X ray reflected by the coal may be corrected and the measuring accuracy may be increased.

In one embodiment, the system may further comprise a detecting box 400 with the X ray device 100 and the X ray measuring devices 200, 201 disposed inside. Therefore, it is possible to prevent an influence of water or dust on the X ray devices 100 and the X ray measuring device 200, 201. In the present disclosure, the distance between the upper surface of the coal 500 and the lower surface of the detecting box 400 is required to ensure that the coal 500 does not collide with the detecting box 400 when the coal 500 has the maximum thickness. However, the nearer the distance is, the more X rays reflected by the coal 500 may be detected, which is beneficial to reduce a statistical fluctuation of counting. Therefore, in one embodiment, the distance between the upper surface of the coal 500 and the lower surface of the detecting box 400 may be chosen to be 2 cm and a shaping device may be provided to make the thickness of the coal 500 stable.

In another embodiment, the system may also further comprise a heating and cooling device 600. The heating and cooling device 600 is disposed in the detecting box 400 and electrically connected with the computing device 300. The computing device 300 controls the heating and cooling device 600 to keep a temperature of the detecting box 400 constant.

Figure 2:
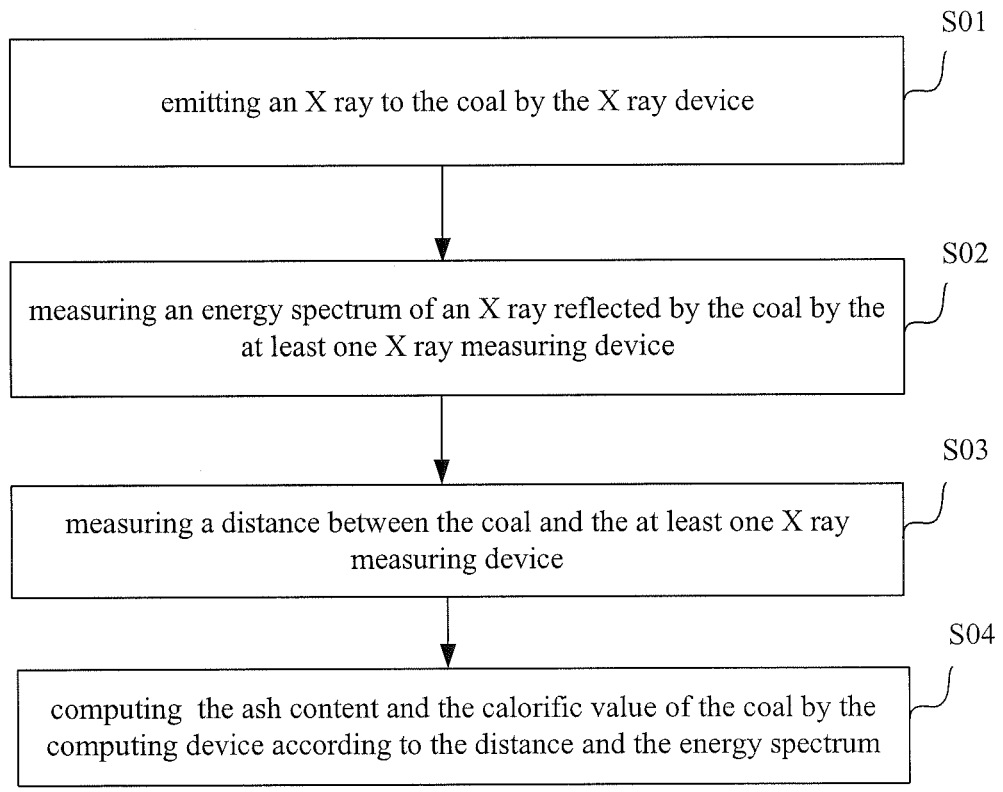
FIG. 2 is a flow chart of a method for measuring the ash content and the calorific value of the coal according to an embodiment of the present disclosure.

A method for measuring an ash content and a calorific value of a coal by the above described system is further provided according to an embodiment of the present disclosure. As shown in FIG. 2, the method comprises the following steps.

In step S01, an X ray is emitted to the coal by the X ray device. In a preferred embodiment, the X ray device emits the bremsstrahlung X ray with the continuous energy.

In step S02, an energy spectrum of an X ray reflected by the coal is measured by the at least one X ray measuring devices. In a preferred embodiment, the at least one X ray measuring device measures energy spectrums of X rays with different energies.

In step S03, a distance between the coal and the at least one X ray measuring device is measured by the distance sensor.

In step S04, the ash content and the calorific value of the coal is computed by the computing device according to the distance and the energy spectrum.

In one embodiment of the present disclosure, the method may further comprise steps of: when a conveyance of the coal on a conveyor belt is suspended, disposing a standard block between the conveyor belt and the X ray device and between the conveyer belt and the at least one X ray measuring device to make the X ray emitted by the X ray device incident on the standard block; measuring an energy spectrum of an X ray reflected by the standard block by the at least one X ray measuring device; and correcting an energy spectrum change of the X ray emitted by the X ray device according to the energy spectrum of the X ray reflected by the standard block. Therefore, the measuring accuracy may be further increased.

Although the method for measuring the ash content and the calorific value of the coal according to the present disclosure is similar to a conventional low-energy gamma ray reflection method in form, there are some essential differences between them. Firstly, the radiation sources are different, in which the low-energy gamma ray reflection method uses the radiogenic isotope as the radiation source, but the method according to the present disclosure uses the X ray device as the radiation source which does not emit the X ray when the power is turned off. Secondly, the radiogenic isotope emits the X ray with a discrete energy, but the X ray device used in the present disclosure emits the X ray with the continuous energy. Thirdly, the X ray with the continuous energy and the one with the discrete energy are completely different in signal detecting and signal processing, because acting laws between the coal and the X rays with different energies are different. As the X ray with the continuous energy overlaps with detected signals, it requires more complex algorithms to separate them. Fourthly, by using the X ray with the continuous energy, it is possible to obtain more composition information of the coal by analysis and calculation, which makes the measurement of the ash content more accuracy. Fifthly, by using the distance sensor to measure the distance between the coal and the X ray measuring devices, the intensity change of the X ray reflected by the coal due to the change of the distance may be corrected and thus the measuring accuracy may be increased.

In addition, the reason why the low-energy gamma ray reflection method is replaced is that it is limited by many factors such as the thickness and a surface topography of the coal. When the thickness of the coal changes, the distance between the surface of the coal and the X ray measuring device changes, and a solid angle formed between the reflection point and the window of the X ray measuring device also changes. Moreover, the X rays reflected by the coal are in every direction. Therefore, the number of X rays incident into the X ray measuring devices changes, which may lead to a measuring error. Furthermore, it can be derived that, under a same thickness fluctuations of the coal, the farther the distance between the X ray measuring device and the conveyor belt is, the weaker the influence of the thickness of the coal is, but meanwhile the less the X rays are detected. Therefore, the statistical error within a same period of time period is increased. However, in the case of measuring the ash content of the coal by the radiogenic isotope, the distance between the radiation source and the coal is not allowed to be changed too much, which limits to reduce the influence of the thickness change of the coal by increasing the distance between the X ray measuring device and the conveyor belt. In addition, as the thickness of the coal usually changes in a great range, an enough distance between the surface of the coal and the X ray measuring device is required to prevent the collision. In another aspect, a counting efficiency of the X ray measuring device will be reduced due to a relative larger distance between the surface of the coal and the X ray measuring device, and thus the measuring accuracy may be reduced. Because the intensity of the X ray emitted by the X ray device used in the present disclosure is much greater than the conventional radiation source used in industry, the above problems do not exist.

In conclusion, with the system and the method for measuring the ash content and the calorific value of the coal according to the present disclosure, a conventional radiation source (such as Pu-238, Am-241, Cs-137 or Ba-133) is replaced with the X ray device, which does not emit any X ray when an power is turned off, and thus a security is improved. Furthermore, by using the X ray with the continuous energy emitted by the X ray device and by measuring the energy spectrums of the X ray with different energies reflected by the coal, an influence of changes of a thickness and a high atomic number element ratio of the coal on the ash content and the calorific value may be corrected, and thus a measuring accuracy may be increased. In addition, by measuring the distance between the coal and the at least one X ray measuring devices by the distance sensor, an influence of a change of the thickness of the coal on the ash content and the calorific value may also be corrected, and thus the measuring accuracy may be further increased.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:
1. A system for measuring an ash content and a calorific value of a coal, comprising:
an X ray device, disposed over the coal and configured to emit an X ray to the coal;

at least one X ray measuring device, disposed over the coal and configured to measure an energy spectrum of an X ray reflected by the coal;

a distance sensor, disposed over the coal and configured to measure a distance between the coal and the at least one X ray measuring device; and a computing device, connected with the at least one X ray measuring device and the distance sensor respectively, and configured to receive the energy spectrum of the X ray reflected by the coal and the distance between the coal and the at least one X ray measuring device and to compute the ash content and the calorific value of the coal according to the energy spectrum and the distance.

2. The system of claim 1, wherein the X ray emitted by the X ray device comprises a bremsstrahlung X ray with a continuous energy.

3. The system of claim 1, further comprising a standard block, wherein during a conveyance of the coal on a conveyer belt, the standard block is taken away to make the X ray emitted by the X ray device directly incident on the coal and to make the X ray reflected by the coal directly reach the at least one X ray measuring device; and when the conveyance of the coal on the conveyer belt is suspended, the standard block is disposed between the conveyer belt and the ray device and between the conveyer belt and the at least one X ray measuring device to make the X ray emitted by the X ray device incident on the standard block so that the at least one X ray measuring device measures an energy spectrum of an X ray reflected by the standard block to correct an energy spectrum change of the X ray emitted by the X ray device.

4. The system of claim 1, wherein the X ray measuring device comprises:

an X ray detector, configured to detect the X ray reflected by the coal and to output a corresponding signal;

a high voltage power source, configured to supply a power to the X ray detector; and a signal collector, configured to receive and reshape the corresponding signal and to generate the energy spectrum of the X ray reflected by the coal according to the corresponding signal.

5. The system of claim 4, wherein the X ray detector comprises any one of a scintillation detector, a proportional counter, a semiconductor detector and a combination thereof.

6. The system of claim 5, wherein a window of the scintillation detector is a beryllium window.

7. The system of claim 5, wherein an energy resolution of the semiconductor detector is larger than 250 eV.

8. The system of claim 4, wherein the signal collector comprises any one of a multi-channel pulse amplitude analyzer, a single-channel pulse amplitude analyzer, a voltage comparator and a combination thereof.

9. The system of claim 1, wherein the X ray device comprises an X ray tube with a working voltage ranging from 10 kV to 200 kV.

10. The system of claim 9, wherein the X ray tube comprises a silver target.

11. The system of claim 1, further comprising a detecting box with the ray device and the at least one X ray measuring device disposed inside.

12. The system of claim 11, wherein a minimum distance between an upper surface of the coal and a lower surface of the detecting box is 2 cm.

13. The system of claim 11, further comprising:

a heating and cooling device, disposed in the detecting box and connected with the computing device, wherein the computing device controls the heating and cooling device to keep a temperature of the detecting box constant.

14. A method for measuring an ash content and a calorific value of a coal by a system, the system comprising an X ray device, at least one X ray detecting device, a distance sensor and a computing device, wherein the X ray device, the at least one X ray measuring device and the distance sensor are disposed over the coal, and the computing device is connected with the at least one X ray measuring device and the distance sensor respectively, and the method comprising steps of:

S01: emitting an X ray to the coal by the X ray device;

S02: measuring an energy spectrum of an X ray reflected by the coal by the at least one X ray measuring device;

S03: measuring a distance between the coal and the at least one X ray measuring device by the distance sensor; and S04: computing the ash content and the calorific value of the coal by the computing device according to the distance and the energy spectrum.

15. The method of claim 14, wherein the X ray emitted by the ray device comprises a bremsstrahlung X ray with a continuous energy.

16. The method of claim 14, further comprising:

when a conveyance of the coal on a conveyor belt is suspended, disposing a standard block between the conveyor belt and the X ray device and between the conveyer belt and the at least one X ray measuring device to make the X ray emitted by the X ray device incident on the standard block;

measuring an energy spectrum of an X ray reflected by the standard block by the at least one X ray measuring device; and correcting an energy spectrum change of the X ray emitted by the X ray device according to the energy spectrum of the X ray reflected by the standard block.

* * * * *